(12) United States Patent
Laminger

(10) Patent No.: US 6,174,312 B1
(45) Date of Patent: Jan. 16, 2001

(54) HELICAL WIRE

(76) Inventor: Karl Laminger, Marktgemeindegasse 63/B 8, A-1230 Vienna (AT)

( * ) Notice: Under 35 U.S.C. 154(b), the term of this patent shall be extended for 0 days.

(21) Appl. No.: 09/341,038

(22) PCT Filed: Nov. 3, 1997

(86) PCT No.: PCT/EP97/06038

§ 371 Date: Jul. 1, 1999

§ 102(e) Date: Jul. 1, 1999

(87) PCT Pub. No.: WO99/22662

PCT Pub. Date: May 14, 1999

(51) Int. Cl.[7] .................................................. A61B 17/04
(52) U.S. Cl. ................................ 606/63; 606/62; 606/78
(58) Field of Search ............................. 606/232, 62, 63, 606/78, 215, 216

(56) References Cited

U.S. PATENT DOCUMENTS 5,626,613  5/1997  Schmieding .................. 606/232

FOREIGN PATENT DOCUMENTS

| 38 35 682 | 4/1990 | (DE) . |
| 94 12 040 | 11/1994 | (DE) . |
| 97 07744 | 3/1997 | (WO) . |

*Primary Examiner*—Gary Jackson
(74) *Attorney, Agent, or Firm*—Nixon & Vanderhye P.C.

(57) ABSTRACT

The invention relates to an osteosynthesis aid for treating upper arm fractures close to the head with an elastically derformable helical wire which is inserted laterally into the medullary space. The helical wire consists e.g. of implant steel wire and is configured as a self-cutting helical spring. The wire is characterized in that it is reversibly deformable in the longitudinal direction by up to 90° over its entire length, for its lateral insertion into the medullary space. The helix becomes elastically braced, forming a three-point brace as it is deformed in the medullary space, and bores itself further into the spongiose bone of the head of humerus. The shape of the osteosynthesis aid advantageously enables the treatment of fractures in oestoporotically altered bone and is also characterized in that the cross-section of the helical spring is triangular, rhomibic or round.

7 Claims, 2 Drawing Sheets

HELICAL WIRE

The invention relates to an osteosynthesis aid for treating upper arm fractures close to the head in the form of an elastically deformable helix capable of being inserted into the medullary space and made, for instance, of implant steel wire, said helix being configured as a self-cutting coil spring.

BACKGROUND OF THE INVENTION

Helical coil springs for treating fractures have already become known from EP 374 088 A1 and DE 38 35 682 A1. In certain cases, the bone substance in which a bore wire is to be inserted is so soft that appropriate fixation is difficult.

It is the object of the invention to provide an osteosynthesis aid for treating upper arm fractures close to the head, which requires little operative expenditures, on the one hand, and ensures sufficient anchorage in the head of humerus, which is soft—in particular with an advanced age—, on the other hand. This object is achieved in that the helix for its lateral insertion into the medullary space is reversibly deformable in the longitudinal direction by up to 90° over its entire length. Said deformability is feasible or possible within an axial or longitudinal distance corresponding to twice the diameter of the helix. Furthermore, the cross section of the helical wire is triangular, rhombic or, in a known manner, round.

As already mentioned above, helically designed coil springs for treating fractures in the shaft region of long tubular bones are known. They stabilize through the long stretched-out contact with the wall of the medullary canal, exhibit a high flexural strength as well as longitudinal rigidity and are introduced in the axial direction in the sense of medullary pins. This is often feasible only by opening adjacent joints, which constitutes a considerable surgical expense and involves the risk of destruction of the articular segment, particularly in the osteoporotic bone. It is clearly less demanding, if the implant can be introduced through an access hole provided in the shaft off joints and fractures. In accordance with the invention, this is achieved in that the helix is imparted special material properties allowing for a uniform reversible variation in the pitch of the thread after introduction, in order to render feasible a change of direction by up to 90°. The helix rigidity resulting from the configuration and material properties, on the other hand, must be so high as to enable a uniform rotary force flux without permanent deformation. As the tip of the helix has reassumed its original form after a directional change, the implant is bored into the spongy bone of the humeral head in the sense of a coreless bone screw designed in the manner of a cork screw.

The deformation remaining at the entry bore hole, which is reversible per se, guarantees the desired protection against implant migration.

BRIEF DESCRIPTION OF THE DRAWINGS

In the following, the invention will be explained in more detail by way of the drawings.

DETAILED DESCRIPTION OF THE DRAWINGS

Figure 6:
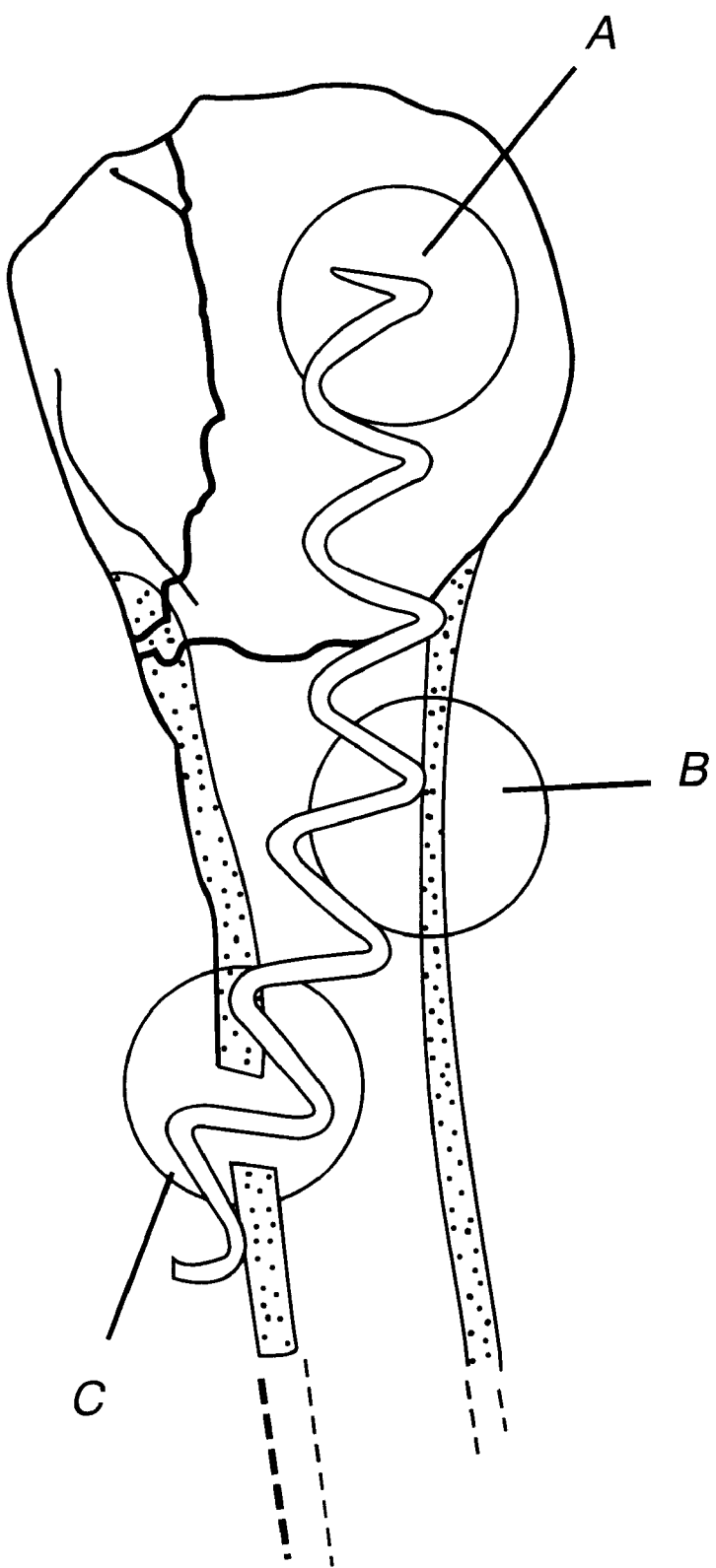
FIG. 6 illustrates the deformation of the wire in the humerus as a result of the three-point bracing.

The helix 1 in the proximal direction is screwed in through a small bore hole laid distally of the fracture on the lateral humeral shaft (FIG. 6, at C) so as to be moved in the proximal direction under elastic deformation, bridging the fracture and, subsequently, boring itself into the spongy bone of the humeral head in a self-cutting helical manner (FIG. 6, at A). By proceeding like that, the helix 1 will be supported on three points in the sense of a spring: 1. in the spongiosa of the humeral head (FIG. 6, at A), 2. on the entry bore hole (FIG. 6, at C) and 3. on the humeral shaft wall opposite the entry bore hole (FIG. 6, at B).

The above-described properties preferably are obtained by using stainless steels such as, e.g., X12CrNi $^{17}/_{7}$ with a wire cross section of 1.4 to 2.2 mm—, and with a helix external diameter of 8 to 14 mm. The following additional dimensions and/or design features are preferred.

Figure 3:
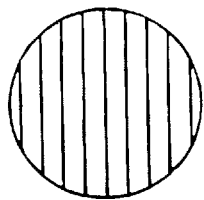
FIGS. 3, 4 and 5 depict different cross sections for the helical wire.
Figure 4:
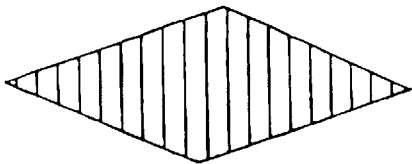
Figure 5:
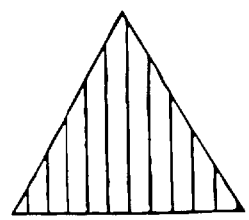

Cross section (Q) of the wire may be round (FIG. 3), rhombic (FIG. 4) or triangular (FIG. 5). The round cross section of the wire avoids peak loads in the bone, yet in terms of guidance offers less favorable properties than the other cross sections mentioned.

Figure 1:
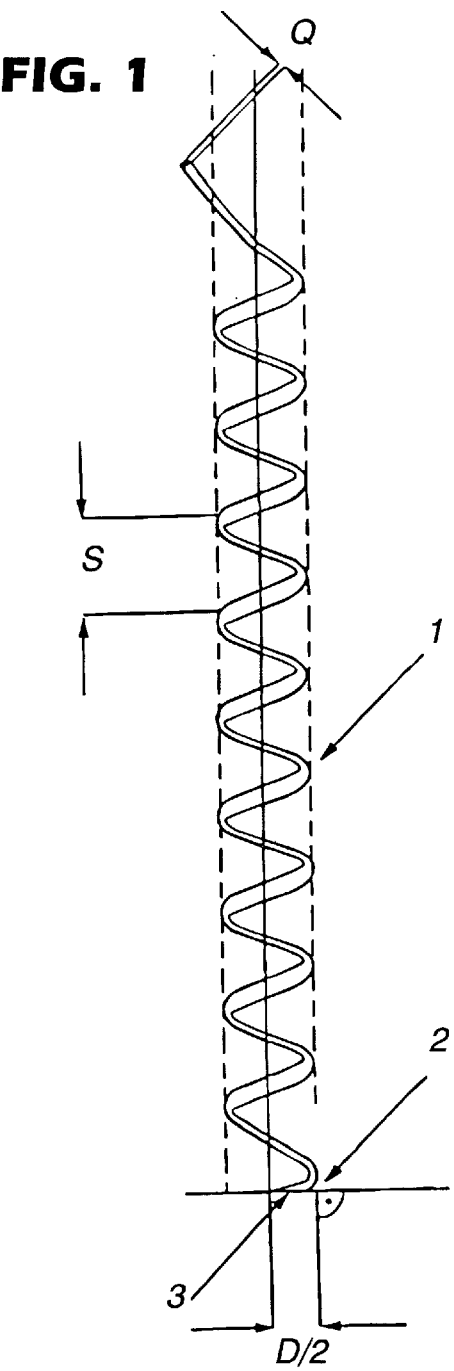
FIG. 1 is a view of the helical wire.
Figure 2:
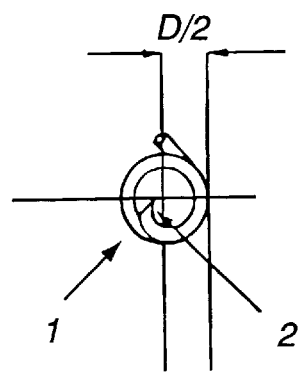
FIG. 2 is a view in the axial direction.

The pitchs of the helix 1 (S) equals, or is larger than (up to a ratio of 1:2.8), half the external diameter (D/2) of the helix 1 (FIGS. 1, 2).

In order to ensure the effect of a three-point bracing (FIG. 6, at A, B, C), a minimum length of the helix 1 of 7.5 cm is required.

The tip 2 of the helical wire or helix 1, irrespective of the cross section employed, must have a ground surface 3 in the direction of the "core" of the helix in order to avoid interlocking on the surface of the medullary canal, on the one hand, and enable boring into the spongiosa of the humeral head, on the other hand (FIG. 6, A).

What is claimed is:

1. An osteosynthesis aid for treating upper arm fractures close to a head portion of a bone, comprising: an elastically deformable wire helix capable of being inserted into the medullary space; said helix being configured as a self-cutting coil spring having a longitudinal axis, said wire helix being reversibly deformable in a longitudinal direction by up to 90° over its entire length.

2. An osteosynthesis aid according to claim 1, wherein a tip of said wire helix is formed with a ground surface extending perpendicular to said longitudinal axis of said wire helix.

3. The osteosynthesis aid of claim 1 wherein said wire helix is round in cross section and further wherein said wire helix is deformable by up to 90° within a longitudinal distance corresponding to twice the diameter of said wire helix.

4. The osteosynthesis aid of claim 3 wherein said wire helix has a pitch equal to or larger than half the diameter of said wire helix.

5. The osteosynthesis aid of claim 1 wherein said wire helix is triangular in cross section.

6. The osteosynthesis aid of claim 1 wherein said wire helix is rhombic shaped in cross section.

7. The osteosynthesis aid of claim 1 wherein said wire helix is comprised of steel.

* * * * *